(12) United States Patent
Zhang et al.

(10) Patent No.: US 11,814,382 B2
(45) Date of Patent: Nov. 14, 2023

(54) CRYSTAL FORM AS ASK1 INHIBITOR AND PREPARATION METHOD AND APPLICATION THEREOF

(71) Applicant: FUJIAN COSUNTER PHARMACEUTICAL CO., LTD., Fujian (CN)

(72) Inventors: Shengbin Zhang, Shanghai (CN); Ning Li, Shanghai (CN); Tao Yu, Shanghai (CN); Yusheng Fu, Shanghai (CN); Jiahu Wu, Shanghai (CN); Chengde Wu, Shanghai (CN)

(73) Assignee: FUJIAN AKEYLINK BIOTECHNOLOGY CO., LTD., Fujian (CN)

( * ) Notice: Subject to any disclaimer, the term of this patent is extended or adjusted under 35 U.S.C. 154(b) by 202 days.

(21) Appl. No.: 17/260,565

(22) PCT Filed: Jul. 19, 2019

(86) PCT No.: PCT/CN2019/096678
§ 371 (c)(1),
(2) Date: Jan. 15, 2021

(87) PCT Pub. No.: WO2020/015721
PCT Pub. Date: Jan. 23, 2020

(65) Prior Publication Data
US 2021/0269441 A1    Sep. 2, 2021

(30) Foreign Application Priority Data
Jul. 20, 2018  (CN) .......................... 201810806190.4

(51) Int. Cl.
C07D 471/04    (2006.01)

(52) U.S. Cl.
CPC ........ *C07D 471/04* (2013.01); *C07B 2200/13* (2013.01)

(58) Field of Classification Search
CPC ...... C07B 2200/13; C07D 471/04; A61P 9/00
See application file for complete search history.

(56) References Cited

FOREIGN PATENT DOCUMENTS

| CN | 102482257 A | 5/2012 |
| CN | 104080771 A | 10/2014 |
| CN | 107108574 A | 8/2017 |
| CN | 107793400 A | 3/2018 |
| CN | 109400625 A | 3/2019 |
| CN | 110698471 A * | 1/2020 | ............. A61K 45/06 |
| CN | 109071538 B | 3/2020 |
| WO | 2011008709 A1 | 1/2011 |
| WO | 2013112741 A1 | 8/2013 |
| WO | 2015187499 A1 | 12/2015 |
| WO | 2016025474 A1 | 2/2016 |
| WO | 2016105453 A1 | 6/2016 |
| WO | 2018133866 A1 | 7/2018 |
| WO | 2018151830 A1 | 8/2018 |
| WO | 2018157856 A1 | 9/2018 |
| WO | 2019034096 A1 | 2/2019 |
| WO | 2020030107 A1 | 2/2020 |

OTHER PUBLICATIONS

The European search report of the corresponding EP patent application No. 19837948.9, dated Oct. 22, 2021.

* cited by examiner

*Primary Examiner* — Joseph K McKane
*Assistant Examiner* — David M Shim
(74) *Attorney, Agent, or Firm* — Gang Yu

(57) ABSTRACT

Provided are crystal forms A, B, C and D of a compound of formula (I), and application of the crystal forms in the preparation of drugs for treating ASK1-related diseases.

16 Claims, 7 Drawing Sheets

CRYSTAL FORM AS ASK1 INHIBITOR AND PREPARATION METHOD AND APPLICATION THEREOF

This application claims the priority of Chinese patent application CN201810806190.4, filed on Jul. 20, 2018, which is incorporated herein by reference in entirety.

TECHNICAL FIELD

The present disclosure relates to crystal forms of a compound of formula (I) and application of the crystal forms of the compound in preparation of drugs for treating ASK1-related diseases.

BACKGROUND

Apoptosis signal-regulating kinase 1 (ASK1) is a member of the mitogen-activated protein kinase kinase kinase (MAP3K) family. ASK1 can be activated by a series of stimuli, such as oxidative stress, reactive oxygen species (ROS), LPS, TNF-a, FasL, endoplasmic reticulum stress and increase in intracellular calcium ion concentration. ASK1 responds to this series of stimuli by activating JNK (c-Jun N-terminal kinase) and p38 MAPK (p38 mitogen-activated protein kinases), and induces multiple apoptosis by signaling involved in mitochondrial cell death pathways. Activation and signaling of ASK1 plays an important role in many diseases, including neurodegenerative diseases, cardiovascular diseases, inflammatory diseases, autoimmune diseases, and metabolic disorders. Therefore, when a patient suffers from neurodegenerative diseases, cardiovascular diseases, inflammation. autoimmune diseases, and metabolic diseases, an ASK1 inhibitor as a therapeutic agent can improve the life of the patient.

SUMMARY

The present disclosure provides crystal form A of a compound of formula (I) having an X-ray powder diffraction (XRPD) pattern with characteristic diffraction peaks at 2θ angles: 8.40±0.2°, 13.46±0.2°, and 14.13±0.2°.

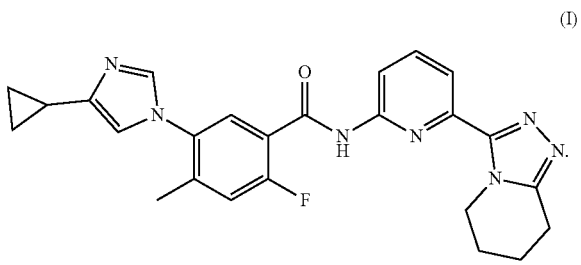 [SMILES: Cc1cc(F)c(C(=O)Nc2cccc(-c3nnc4n3CCCC4)n2)cc1-n1cnc(C2CC2)c1]

(I)

In some embodiments of the present disclosure, the above crystal form A has an X-ray powder diffraction pattern with characteristic diffraction peaks at 2θ angles: 8.40±0.2°, 10.56±0.2°, 13.46±0.2°, 14.13±0.2°, 15.31±0.2°, 16.79±0.2°, 24.09±0.2° and 24.97±0.2°.

In some embodiments of the present disclosure, the above crystal form A has a XRPD pattern as shown in FIG. 1.

In some embodiments of the present disclosure, the above crystal form A has XRPD pattern resolution data as shown in Table 1:

TABLE 1

XRPD pattern resolution data for crystal form A

| No. | 2θ Angle (°) | Interplanar Distance (Å) | Intensity |
|---|---|---|---|
| 1 | 8.402 | 10.5154 | 2209 |
| 2 | 10.555 | 8.3748 | 961 |
| 3 | 13.456 | 6.5749 | 2133 |
| 4 | 14.126 | 6.2645 | 3260 |
| 5 | 15.308 | 5.7833 | 439 |
| 6 | 16.794 | 5.2749 | 486 |
| 7 | 17.4 | 5.0925 | 232 |
| 8 | 17.959 | 4.9352 | 332 |
| 9 | 18.515 | 4.7883 | 81 |
| 10 | 19.314 | 4.5919 | 90 |
| 11 | 19.671 | 4.5093 | 186 |
| 12 | 20.466 | 4.3359 | 112 |
| 13 | 21.152 | 4.1968 | 196 |
| 14 | 22.299 | 3.9834 | 94 |
| 15 | 23.201 | 3.8306 | 175 |
| 16 | 23.621 | 3.7635 | 391 |
| 17 | 24.089 | 3.6913 | 454 |
| 18 | 24.508 | 3.6292 | 648 |
| 19 | 24.966 | 3.5636 | 740 |
| 20 | 25.792 | 3.4513 | 84 |
| 21 | 26.107 | 3.4105 | 166 |
| 22 | 26.542 | 3.3555 | 369 |
| 23 | 27.212 | 3.2743 | 172 |
| 24 | 28.277 | 3.1535 | 118 |
| 25 | 28.636 | 3.1148 | 155 |
| 26 | 30.166 | 2.9601 | 78 |
| 27 | 30.79 | 2.9015 | 69 |
| 28 | 31.238 | 2.8609 | 49 |
| 29 | 32.088 | 2.7871 | 59 |
| 30 | 32.838 | 2.7251 | 68 |
| 31 | 33.938 | 2.6393 | 54 |
| 32 | 36.332 | 2.4706 | 78 |

In some embodiments of the present disclosure, the above crystal form A has a differential scanning calorimetry curve (DSC) with two starting points of endothermic peaks at 210.78° C. and 237.74° C., respectively; and an exothermic peak at 215.70° C.

In some embodiments of the present disclosure, the above crystal form A has a DSC thermogram as shown in FIG. 2.

In some embodiments of the present disclosure, the above crystal form A has a thermogravimetric analysis curve (TGA) with a weight loss of 1.799% at 120° C.

In some embodiments of the present disclosure, the above crystal form A has a TGA thermogram as shown in FIG. 3.

The present disclosure provides crystal form B of a compound of formula (I) having an X-ray powder diffraction pattern with characteristic diffraction peaks at 2θ angles: 8.85±0.2°, 17.07±0.2°, and 17.70±0.2°.

In some embodiments of the present disclosure, the above crystal form B has an X-ray powder diffraction pattern with characteristic diffraction peaks at 2θ angles of: 8.85±0.2°, 10.20±0.2°, 14.62±0.2°, 17.07±0.2°, 17.70±0.2°, 21.57±0.2°, 23.34±0.2° and 24.37±0.2°.

In some embodiments of the present disclosure, the above crystal form B has a XRPD pattern as shown in FIG. 4.

In some embodiments of the present disclosure, the above crystal form B has XRPD pattern resolution data shown in Table 2:

TABLE 2

XRPD pattern resolution data for crystal form B

| No. | 2θ Angle (°) | Interplanar Distance (Å) | Intensity |
|---|---|---|---|
| 1 | 8.061 | 10.9596 | 209 |
| 2 | 8.852 | 9.9819 | 943 |
| 3 | 9.534 | 9.2686 | 70 |
| 4 | 10.2 | 8.6652 | 448 |
| 5 | 11.203 | 7.8917 | 217 |
| 6 | 11.5 | 7.6882 | 99 |
| 7 | 12.406 | 7.1287 | 266 |
| 8 | 12.878 | 6.8686 | 209 |
| 9 | 14.62 | 6.0537 | 357 |
| 10 | 15.187 | 5.829 | 117 |
| 11 | 15.666 | 5.6521 | 145 |
| 12 | 17.068 | 5.1906 | 811 |
| 13 | 17.697 | 5.0075 | 1165 |
| 14 | 18.941 | 4.6813 | 215 |
| 15 | 19.674 | 4.5086 | 245 |
| 16 | 21.567 | 4.1169 | 610 |
| 17 | 22.457 | 3.9559 | 556 |
| 18 | 23.344 | 3.8074 | 573 |
| 19 | 24.371 | 3.6493 | 553 |
| 20 | 25.278 | 3.5204 | 287 |
| 21 | 25.867 | 3.4416 | 257 |
| 22 | 26.698 | 3.3363 | 115 |
| 23 | 28.197 | 3.1622 | 325 |
| 24 | 31.689 | 2.8213 | 108 |
| 25 | 34.632 | 2.588 | 50 |

In some embodiments of the present disclosure, the above crystal form B has a differential scanning calorimetry curve (DSC) with onsets of endothermic peaks at 149.17° C., 170.25° C. and 237.84° C., respectively; and an exothermic peak at 177.34° C.

In some embodiments of the present disclosure, the above crystal form B has a DSC thermogram as shown in FIG. 5.

In some embodiments of the present disclosure, the above crystal form B has a thermogravimetric analysis curve (TGA) with a weight loss up to 0.3593% at 60° C., and a weight loss up to 1.5703% at 120° C.

In some embodiments of the present disclosure, the above crystal form B has a TGA thermogram as shown in FIG. 6.

The present disclosure provides crystal form C of a compound of formula (I) having an X-ray powder diffraction pattern with characteristic diffraction peaks at 2θ angles: 9.47±0.2°, 16.45±0.2°, and 17.32±0.2°.

In some embodiments of the present disclosure, the above crystal form C has an X-ray powder diffraction pattern with characteristic diffraction peaks at 2θ angles: 8.72±0.2°, 9.47±0.2°, 10.44±0.2°, 13.75±0.2°, 16.45±0.2°, 17.32±0.2°, 19.41±0.2° and 26.82±0.2°.

In some embodiments of the present disclosure, the above crystal form C has a XRPD pattern as shown in FIG. 7.

In some embodiments of the present disclosure, the above crystal form C has XRPD pattern resolution data as shown in Table 3:

TABLE 3

XRPD pattern resolution data for crystal form C

| No. | 2θ Angle (°) | Interplanar Distance (Å) | Intensity |
|---|---|---|---|
| 1 | 8.205 | 10.7673 | 241 |
| 2 | 8.719 | 10.133 | 1025 |
| 3 | 9.472 | 9.329 | 13948 |
| 4 | 10.435 | 8.4703 | 958 |
| 5 | 10.807 | 8.1795 | 256 |
| 6 | 11.681 | 7.5695 | 398 |
| 7 | 12.728 | 6.9491 | 142 |
| 8 | 13.751 | 6.4345 | 1235 |
| 9 | 15.629 | 5.6653 | 584 |
| 10 | 16.452 | 5.3836 | 2645 |
| 11 | 17.323 | 5.1148 | 1761 |
| 12 | 17.837 | 4.9685 | 285 |
| 13 | 19.02 | 4.6621 | 694 |
| 14 | 19.413 | 4.5686 | 1293 |
| 15 | 20.009 | 4.4339 | 420 |
| 16 | 20.754 | 4.2763 | 522 |
| 17 | 21.167 | 4.1938 | 595 |
| 18 | 21.744 | 4.0838 | 883 |
| 19 | 22.533 | 3.9426 | 745 |
| 20 | 23.755 | 3.7424 | 1043 |
| 21 | 24.07 | 3.6942 | 247 |
| 22 | 24.903 | 3.5725 | 859 |
| 23 | 25.809 | 3.4491 | 1465 |
| 24 | 26.815 | 3.3219 | 1543 |
| 25 | 28.356 | 3.1448 | 827 |
| 26 | 29.74 | 3.0016 | 319 |
| 27 | 30.39 | 2.9388 | 266 |
| 28 | 30.783 | 2.9022 | 143 |
| 29 | 31.515 | 2.8364 | 80 |
| 30 | 33.863 | 2.6449 | 157 |

In some embodiments of the present disclosure, the above crystal form C has a differential scanning calorimetry curve with three starting points of endothermic peaks at 105.76° C., 171.54° C. and 237.48° C., respectively; and an exothermic peak at 177.64° C.

In some embodiments of the present disclosure, the above crystal form C has a DSC thermogram as shown in FIG. 8.

In some embodiments of the present disclosure, the above crystal form C has a thermogravimetric analysis curve with a weight loss up to 1.115% at 75.89° C., and a weight loss up to 2.958% at 164.93° C.

In some embodiments of the present disclosure, the above crystal form C has a TGA thermogram as shown in FIG. 9.

The present disclosure provides crystal form D of a compound of formula (I) having an X-ray powder diffraction pattern with characteristic diffraction peaks at 2θ angles: 10.26±0.2°, 12.73±0.2°, and 20.60±0.2°.

In some embodiments of the present disclosure, the above crystal form D has an X-ray powder diffraction pattern with characteristic diffraction peaks at 2θ angles: 10.26±0.2°, 11.84±0.2°, 12.73±0.2°, 14.70±0.2°, 16.39±0.2°, 20.60±0.2°, 21.22±0.2° and 22.26±0.2°.

In some embodiments of the present disclosure, the above crystal form D has a XRPD pattern as shown in FIG. 10.

In some embodiments of the present disclosure, the above crystal form D has XRPD pattern resolution data as shown in Table 4:

TABLE 4

XRPD pattern resolution data for crystal form D

| No. | 2θ Angle (°) | Interplanar Distance (Å) | Intensity |
|---|---|---|---|
| 1 | 4.633 | 19.0574 | 233 |
| 2 | 7.965 | 11.0913 | 277 |
| 3 | 9.271 | 9.5316 | 418 |

TABLE 4-continued

XRPD pattern resolution data for crystal form D

| No. | 2θ Angle (°) | Interplanar Distance (Å) | Intensity |
|---|---|---|---|
| 4 | 10.258 | 8.6159 | 9078 |
| 5 | 11.122 | 7.9485 | 590 |
| 6 | 11.838 | 7.4697 | 1224 |
| 7 | 12.725 | 6.9506 | 5077 |
| 8 | 14.697 | 6.0223 | 2253 |
| 9 | 15.073 | 5.8729 | 288 |
| 10 | 15.964 | 5.547 | 223 |
| 11 | 16.394 | 5.4025 | 883 |
| 12 | 17.664 | 5.0168 | 345 |
| 13 | 18.232 | 4.862 | 191 |
| 14 | 19.645 | 4.5152 | 154 |
| 15 | 20.168 | 4.3993 | 368 |
| 16 | 20.6 | 4.308 | 4379 |
| 17 | 21.216 | 4.1844 | 1102 |
| 18 | 22.257 | 3.9908 | 3979 |
| 19 | 23.34 | 3.8081 | 281 |
| 20 | 23.837 | 3.7297 | 269 |
| 21 | 24.37 | 3.6494 | 1581 |
| 22 | 24.864 | 3.578 | 283 |
| 23 | 25.752 | 3.4567 | 158 |
| 24 | 26.247 | 3.3925 | 557 |
| 25 | 26.759 | 3.3288 | 522 |
| 26 | 28.219 | 3.1598 | 157 |
| 27 | 28.97 | 3.0796 | 357 |
| 28 | 29.661 | 3.0093 | 212 |
| 29 | 31.142 | 2.8696 | 113 |
| 30 | 33.156 | 2.6997 | 334 |
| 31 | 33.466 | 2.6754 | 199 |
| 32 | 35.112 | 2.5537 | 136 |
| 33 | 36.11 | 2.4853 | 98 |
| 34 | 39.176 | 2.2976 | 67 |

In some embodiments of the present disclosure, the above crystal form D has a differential scanning calorimetry curve with onsets of endothermic peaks at 101.92° C., 171.01° C. and 237.29° C., respectively; and an exothermic peak at 179.96° C.

In some embodiments of the present disclosure, the above crystal form D has a DSC thermogram as shown in FIG. 11.

In some embodiments of the present disclosure, the above crystal form D has a thermogravimetric analysis curve a weight loss up to 0.4876% at 75.62° C., and a weight loss up to 2.5836% at 132.36° C.

In some embodiments of the disclosure, the above crystal form D has a TGA thermogram as shown in FIG. 12.

The present disclosure also provides application of crystal form A, crystal form B, crystal form C or crystal form D in the preparation of drugs for treating ASK1-related diseases.

Technical Effects

Crystal form A, crystal form B, crystal form C or crystal form D of the compound disclosed by the present disclosure are stable, are less affected by light, heat and humidity, have very high solubility, and have broad prospects for preparing medicines.

Definitions and Descriptions

As used herein, the following terms and phrases are intended to have the following meanings, unless otherwise indicated. A specific phrase or term should not be considered uncertain or unclear without a special definition, but should be understood in its ordinary meaning. When a trade name appears herein, it is intended to refer to its corresponding product or its active ingredient.

The intermediate compounds of the present disclosure can be prepared by a variety of synthetic methods well known to those skilled in the art, including the specific embodiments listed below, the embodiments formed by combining them with other chemical synthesis methods, and equivalent alternatives well known to those skilled in the art. Preferred embodiments include but are not limited to the examples of the present disclosure.

The chemical reactions of specific embodiments of the present disclosure are carried out in a suitable solvent that is suitable for the chemical variations of the present disclosure and the reagents and materials required therefor. In order to obtain the compounds of the present disclosure, it is sometimes necessary for a person skilled in the art to modify or select the synthetic steps or reaction schemes on the basis of the existing embodiments.

The present disclosure will be specifically described below through examples, and these examples are not meant to limit the present disclosure in any way.

All solvents used in the present disclosure are commercially available without further purification.

The solvents used in the present disclosure can be obtained commercially. The present disclosure uses the following acronyms: DCM stands for dichloromethane; DMF stands for N,N-dimethylformamide; DMSO stands for dimethyl sulfoxide; EtOH stands for ethanol; MeOH stands for methanol; TFA stands for trifluoroacetic acid; TsOH stands for p-toluenesulfonic acid; mp stands for the melting point; $EtSO_3H$ stands for ethanesulfonic acid; $MeSO_3H$ stands for methanesulfonic acid; ATP stands for adenosine triphosphate; HEPES stands for 4-hydroxyethylpiperazine ethanesulfonic acid; EGTA stands for ethylene glycol bis(2-amino ethyl ether) tetraacetic acid; $MgCl_2$ stands for magnesium dichloride; $MnCl_2$ stands for manganese dichloride; DTT stands for dithiothreitol; DCC stands for dicyclohexylcarbodiimide; DMAP stands for 4-dimethylaminopyridine; DIEA stands for N,N-Diisopropylethylamine; and wt %: mass percentage.

The Powder X-Ray Powder Diffractometer (XRPD) Method of the Present Disclosure

Instrument Model: Bruker D8 advance X-ray diffractometer

Test Method: approximately 10-20 mg of sample was used for XRPD detection.

Detailed XRPD parameters were as follows:
Tube: Cu, kα, (λ=1.54056 Å)
Voltage: 40 kV, Current: 40 mA
Div. slit: 0.60 mm
Det. slit: 10.50 mm
Antis. slit: 7.10 mm
Scan range: 3 or 4-40 deg
Step: 0.02 deg
Time: 0.12 seconds
Sample disk rotation speed: 15 rpm The Differential Scanning Calorimeter (DSC) Method of the Present Disclosure Instrument Model: TADSCQ2000 Differential Scanning calorimeter Test Method: a sample (0.5-1 mg) was taken and placed in a DSC aluminum pan for testing. The sample was heated from 25° C. (room temperature) to 300° C. (or 350° C.) at a heating rate of 10° C./min.

Thermal Gravimetric Analyzer (TGA) Method of the Present Disclosure

Instrument Model: TAQ5000 Thermogravimetric Analyzer Test Method: a sample (2-5 mg) was taken and placed in a TGA platinum pan for testing. The sample was heated from room temperature to 350° C. or 20% weight loss under the condition of 25 mL/min $N_2$ and at a heating rate of 10° C./min.

DETAILED DESCRIPTION OF THE EMBODIMENTS

Figure 1:
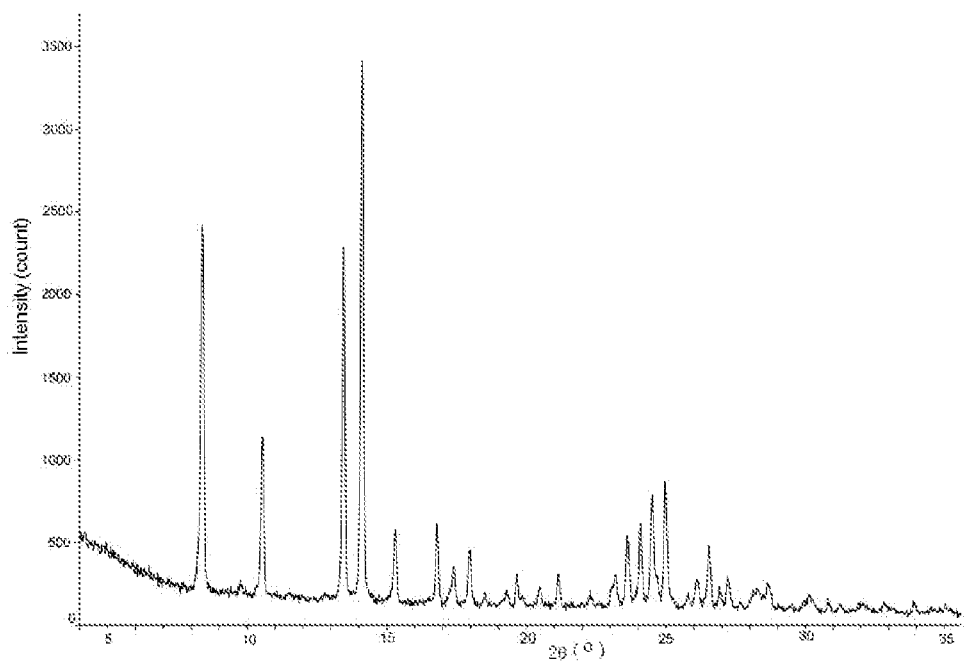
FIG. 1 is an XRPD pattern of Cu-Kα radiation of crystal form A of compound (I)

For a better understanding of the present disclosure, reference will now be made to the following detailed description taken in conjunction with specific embodiments, which, however, should not be taken in a limiting sense.

Example 1: Preparation of Compound of Formula (I)

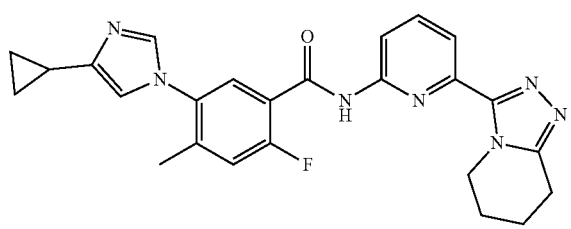

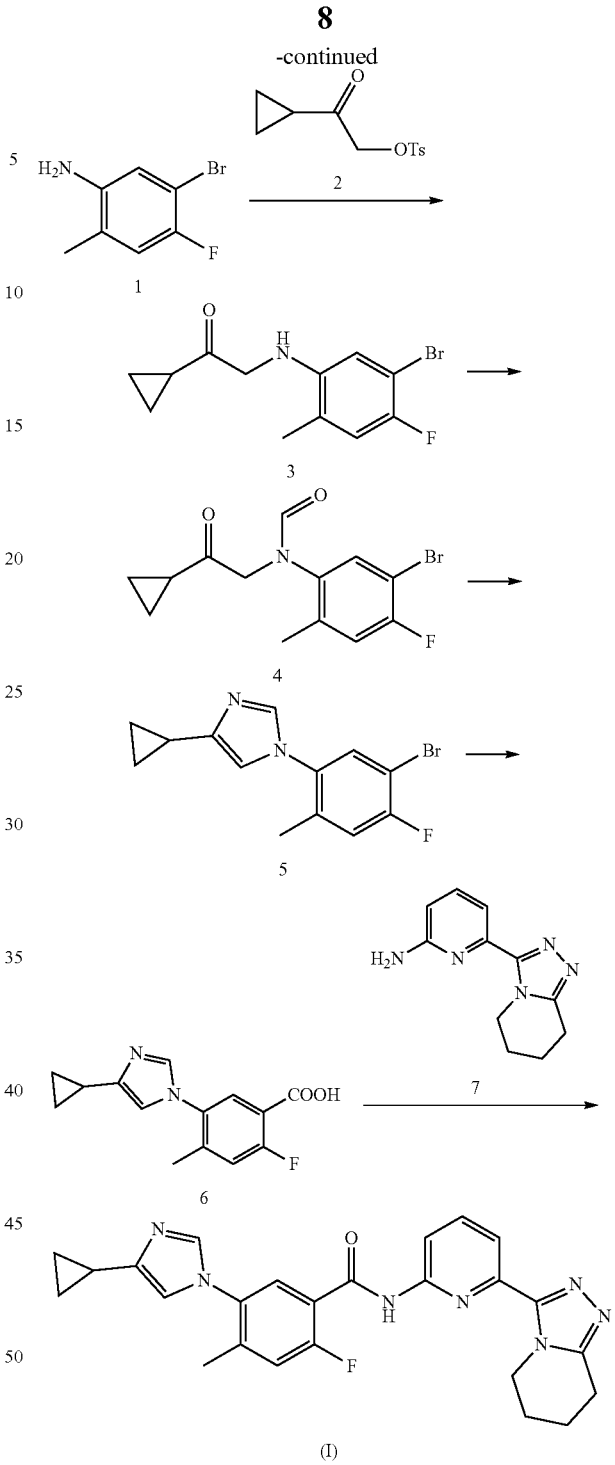

Step 1:

Compound 1 (370 g, 1.81 mol, 1 eq) and compound 2 (513 g, 1.99 mol, 1.1 eq, 98.71% purity) were added to a dry 5 L three-necked flask. Toluene (1.85 L) and DIEA (665.00 nit, 3.81 mol, 2.1 eq) were added sequentially to the reaction flask. The reaction system was slowly warmed to 100° C. and stirred for 10 hours. The reaction liquid was cooled to room temperature, added with water and stirred. The mixture was allowed to stand and separated to collect the organic phase. The collected organic phase was washed sequentially with $NH_4Cl$ (27 wt %, 1 L), $NaHCO_3$ (9 wt %, 1 L) and NaCl (15 wt %, 500 mL), then dried over anhydrous sodium sulfate (150 g), and filtered. The filtrate was spin-dried under reduced pressure (oil pump, 50° C.) to give a grey solid (498 g). The grey solid was slurried with n-hexane (1 L) at room temperature for 2 hours, and filtered. The filter cake was spin-dried under reduced pressure (oil pump, 50° C.) to give compound 3.

$^1$H NMR (400 MHz, DMSO-$d_6$) ppm 0.86-0.90 (m, 2H), 0.91-0.96 (m, 2H), 2.09 (s, 3H), 2.14-2.21 (m, 1H), 4.16 (d, J=5.52 Hz, 2H) 5.27 (d, J=5.52 Hz, 1H), 6.50 (d, J=6.02 Hz, 1H), 7.05 (d, J=9.29 Hz, 1H).

Step 2:

Acetic anhydride (540.00 mL, 5.77 mol, 4 eq) and formic acid (1.84 L) were added to a dry 5 L three-necked flask, then the temperature of a reaction solution in the three-necked flask was reduced to 0° C. Compound 3 (460.00 g, 1.44 mol, 1 eq, purity 89.37%) was dissolved in anhydrous dichloromethane (1.84 L) and added to the reaction solution, and the reaction solution in the three-necked flask was stirred at 0° C. for 1 hour. Water (1 L) was added into the three-necked flask, and pH value is adjusted to 8-9 by NaOH (50%). The temperature of the reaction solution in the three-necked flask was kept at 0-15° C. An organic phase was collected. The collected organic phase was washed by dichloromethane (1.5 L) and saturated sodium chloride (1 L) in sequence, dried over anhydrous sodium sulfate (200 g), and filtered. The filtrate was spin-dried under reduced pressure (water pump, 50° C.) to give compound 4.

1H NMR (400 MHz, DMSO-$d_6$) δ ppm 0.86-0.90 (m, 2H), 0.93-0.96 (m, 2H), 2.06-2.10 (m, 1H), 2.25 (s, 3H), 4.68 (s, 2H), 7.41 (d, J=9.54 Hz, 1H) 7.61 (d, J=6.78 Hz, 1H), 8.17 (s, 1H).

Step 3:

Compound 4 (440 g, 1.33 mol, 1 eq, 94.77% purity) was added to a dry 5 L three-necked flask. Acetic acid (2.2 L) and ammonium acetate (399.03 g, 5.18 mol, 3.9 eq) were added sequentially to the three-necked flask. A reaction solution in the three-necked flask was slowly warmed to 115° C. and stirred for 43 h. One drop of the reaction solution was dissolved in 1 mL of methanol and sent to LCMS which showed 24.50% of the starting compound 4 remained and 70.67% of the product was formed. Additional ammonium acetate (102.00 g, 1.32 mol L, 1 eq) was added to the three-necked flask and the reaction solution was stirred for 20 hours. One drop of the reaction solution was dissolved in 1 mL of methanol and sent to LCMS which showed 12.66% of the starting compound 4 remained and 76.03% of the product was formed. Additional ammonium acetate (51.00 g, 661.63 mol L, 0.5 eq) was added and the reaction system was continued to be stirred for 15 hours. One drop of the reaction solution was dissolved in 1 mL of methanol and sent to LCMS which showed 7.32% of the starting compound 4 remained and 89.36% of the product was formed. Water (1 L) was added the three-necked flask, then isopropyl acetate (1 L) is added, and stirred. A mixture in the three-necked flask was allowed to stand and separated to collect an organic phase. The collected organic phase was adjusted the pH value to 8-9 by NaOH (50%). The mixture was allowed to stand and separated to collect an organic phase. The organic phase was washed with saturated NaCl (800 mL), dried over anhydrous sodium sulfate (200 g), and filtered. The filtrate was spin-dried under reduced pressure (water pump, 50° C.) to give a tan oily liquid (420 g). The tan oily liquid was dissolved in methyl tert-butyl ether (600 mL), and then n-hexane (600 mL) was slowly added to the solution until no further precipitation appeared. The upper layer of the solution became yellow clear, and filtered. The filtrate was spin-dried under reduced pressure (water pump, 50° C.) to give compound 5. $^1$H NMR (400 MHz, DMSO-$d_6$) δ ppm 0.66-0.71 (m, 2H), 0.76-0.81 (m, 2H), 1.78-1.86 (m, 1H), 2.13 (s, 3H), 7.13 (d, J=1.25 Hz, 1H), 7.47 (d, J=9.54 Hz, 1H), 7.64 (d, J=1.25 Hz, 1H), 7.69 (d, J=6.53 Hz, 1H).

Step 4:

Compound 5 (80 g, 238.63 mmoL, 1 eq, 88.04% purity) was added to a dry 3 L three-necked flask, and anhydrous tetrahydrofuran (1.20 L) was added to the three-necked flask. The air in the system was replaced with a nitrogen balloon, and the operation was repeated twice. The temperature of a reaction solution in the three-necked flask was reduced to 0° C. iPrMgCl (143.00 mL, 286.36 mmoL, 1.2 eq, 2 M) was added slowly, and stirred for 2 hours. CO2 (15 Psi) was introduced into the three-necked flask for 30 minutes, then the ice bath was removed, and CO2 (15 Psi) was introduced at room temperature for 60 minutes to stop the reaction. Water (1 L) was added into the reaction solution, then concentrated (water pump, 50° C.) to obtain a yellow liquid (1.2 L). Methyl tert-butyl ether (1 L) was added into the reaction solution, and stirred. The mixture was allowed to stand and separated to collect an aqueous phase. The collected aqueous phase was adjusted the pH value to 4-5 by 6 M HCl, and added with methyl tert-butyl ether (1 L) for extraction; the aqueous phase was collected and concentrated with a water pump (70° C.) to a volume of 400 mL. The solution was cooled, and allowed to stand to precipitate a solid. The mixture was combined into another batch (130 g charge) of the mixture and filtered. The filter cake was spin-dried under reduced pressure (water pump, 50° C.) to give compound 6.

1H NMR (400 MHz, DMSO-$d_6$) δ ppm 0.86-0.91 (m, 2H), 1.00-1.06 (m, 2H), 2.00-2.07 (m, 1H), 2.25 (s, 3H), 7.54 (d, J=11.29 Hz, 1H), 7.75 (d, J=1.00 Hz, 1H), 8.00 (d, J=6.78 Hz, 1H), 9.31 (d, J=1.51 Hz, 1H).

Step 5:

Compound 6 (70 g, 260.57 mmol, 1.1 eq.) was placed in DCM (700 L), and DMF (2 mL, 25.99 mmol, 0.1 eq.) was added as a reaction solution. (COCl)$_2$ (35.5 mL, 405.55 mmol, 1.7 eq.) was added dropwise under stirring to the reaction solution and the reaction solution was stirred at 30° C. for 1 h. The reaction solution was completely clear and spun under reduced pressure to about 200 mL. The reaction solution was added with 500 mL of anhydrous DCM, and spun under reduced pressure to about 200 mL again. The operation was repeated twice. To the reaction solution, anhydrous DCM 700 mL, compound 7 (51 g, 236.93 mmol, 1 eq), DIEA (41.5 mL, 237.61 mmol, 1 eq) were added, and the reaction solution was stirred at 30° C. for 1 h. The reaction solution was poured into 2 L of water along with another batch (same charge) of reaction solution, and extracted with DCM (1 L×3). The organic phases were combined, then washed with water (2 L), saturated NaHCO$_3$ (2 L) and water (2 L), dried over anhydrous magnesium sulfate, and filtered. The filtrate was spin-dried under reduced pressure to obtain a crude product. Acetonitrile (170 mL) was added into the crude product, and fully shaken uniformly to precipitate a large amount of solid. Acetonitrile (170 mL) was added again, stirred for 30 min at normal temperature, and filtered. The filter cake was washed with 500 mL acetonitrile, collected, and dried to obtain 115.5 g of a white solid product. The 115.5 g of solid was combined with another batch of 76.5 g of product, and dissolved in HCl solution (120 mL, 0.7 mol/L). Followed by addition of 6 mol/L NaOH aqueous solution under stirring, a large amount of solid precipitated out, and filtered. The filter cake was collected, placed in 1 L of water and stirred vigorously for 30 min, and filtered. The filter cake was washed with 500 mL of water, and dried at 70° C. to obtain the compound of formula (I).

$^1$H NMR (400 MHz, deuterochloroform) δ ppm 0.81-0.84 (m, 2H), 0.87-0.92 (m, 2H), 1.87-1.93 (m, 1H), 1.97-1.98 (m, 2H), 2.03-2.06 (m, 2H), 2.29 (s, 3H), 3.07-3.10 (m, 2H), 4.47-4.50 (m, 2H), 6.79 (d, J=0.75 Hz, 1H), 7.19 (d, J=12.30 Hz, 1H), 7.44 (d, J=1.00 Hz, 1H), 7.89 (J=8.03 Hz, 1H), 8.06 (J=7.53 Hz, 2H), 8.35 (d, J=8.28 Hz, 1H), 9.04 (d, J=14.81 Hz, 1H).

Example 2: Preparation of Crystal Form A of Compound of Formula (I)

Approximately 50 mg of the compound of formula (I) was weighed and placed into a sample vial, and 400 μL acetone (or acetonitrile) was added to become a suspension. The suspension was shaken continuously for 3 days at 40° C. and centrifuged. The residual solid was placed in a vacuum oven and dried overnight under vacuum at 30° C. to obtain crystal form A of the compound of formula (I).

Example 3: Preparation of Crystal Form B of Compound of Formula (I)

Approximately 50 mg of the compound of formula (I) was weighed and placed into a sample vial, and 210 μL methanol was added to become a suspension. The suspension was shaken continuously for 3 days at 40° C. and centrifuged. The residual solid was placed in a vacuum oven and dried overnight under vacuum at 30° C. to obtain crystal form B of the compound of formula (I).

Example 4: Preparation of Crystal Form C of Compound of Formula (I)

Approximately 50 mg of the compound of formula (I) was weighed and placed into a sample vial, and 200 μL ethanol was added to become a suspension. The suspension was shaken continuously for 3 days at 40° C. and centrifuged. The residual solid was placed in a vacuum oven and dried overnight under vacuum at 30° C. to obtain crystal form C of the compound of formula (I).

Example 5: Preparation of Crystal Form D of Compound of Formula (I)

Approximately 50 mg of the compound of formula (I) was weighed and placed into a sample vial, and 200 μL ethanol/water mixture (ethanol:water=3:1) was added to become a suspension. The suspension was shaken continuously for 3 days at 40° C. and centrifuged. The residual solid was placed in a vacuum oven and dried overnight under vacuum at 30° C. to obtain crystal form D of the compound of formula (I).

Example 6: Solid Stability Test of Crystal Form a of Compound of Formula (I)

The stability of compound A of formula (I) under the conditions of high temperature (60° C., open), high humidity (room temperature/relative humidity 92.5%, open) and strong light (5000 lx, closed) was investigated according to the "The Guideline for Stability Testing of Drug Substances and Products" (ChP 2015<9001>).

About 1 g of crystal form A of the compound of formula (I) was weighed, and spread in an open clean weighing bottle. The samples were respectively placed in a high-temperature, high-humidity and strong-light storage container. The samples were taken at 5 and 10 days after placing, and the test results were compared with the initial test results at 0 days. The test results are shown in Table 5.

TABLE 5

Solid stability test results of crystal form A of compound of formula (I)

| Experimental Conditions | Timing | Crystal form |
| --- | --- | --- |
| — | Day 0 | Crystal form A |
| High Temperature (60° C., Open) | Day 5 | Crystal form A |
|  | Day 10 | Crystal form A |
| High Humidity (25° C./Relative Humidity 90%, Open) | Day 5 | Crystal form A |
|  | Day 10 | Crystal form A |
| Strong light (5000 1x, closed) | Day 5 | Crystal form A |
|  | Day 10 | Crystal form A |

Conclusion: crystal form A of the compound of formula (I) has good stability under the conditions of high temperature, high humidity and strong light.

Figure 13:
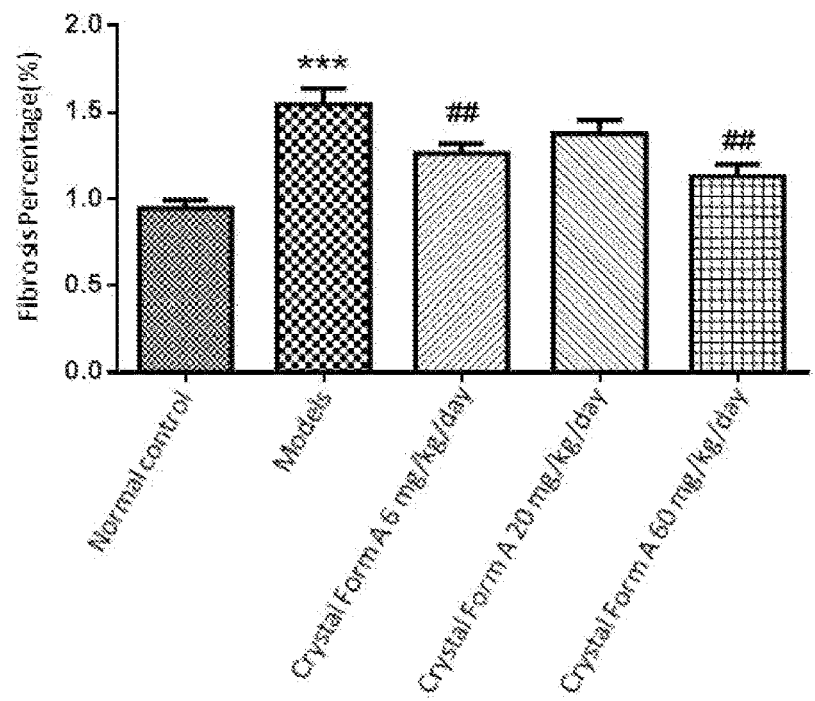
FIG. 13 is a result of an in vivo efficacy test of crystal form A of compound (I) in an MCD-induced mouse NASH model; note: * indicates p<0.001 vs. normal control group; ##indicates p<0.01 vs. model group.

Effect Example 1 In Vivo Efficacy Test of Crystal Form A of Compound of Formula (I) in MCD-Induced Mouse NASH Model Experimental Materials:
SPF grade C57BL/6 male mice, 22-25 grams in weight.
MCD: methionine/choline deficient feed.
Liver Propylene Analytical Reagents: hematoxylin dyeing liquid, eosin dyeing liquid and Picro sirius dyeing liquid.
Experimental Method:
After the animals were adapted for one week in the facility, the normal control group was still fed with the normal feed, and other animals were fed with MCD feed instead. The drinking water didn't change and the feed was replaced once every 48 hours. Beginning at week 5, the remaining groups, except the normal control and model groups, were administrated with subject compound. The Experiment lasted for a total of 8 weeks. At the end of the experiment, animal liver samples were collected for histopathological analysis. Whether the molding is successful is determined by comparing a model group with a normal control group; and whether the drug shows a drug effect is determined by comparing the administration group and the model group. The experimental results are shown in FIG. 13.
Experimental Conclusion:
Crystal form A of compound of formula (I) (6 mg/Kg BID and 60 mg/Kg BID) has a significant effect on improving liver fibrosis.

Figure 14:
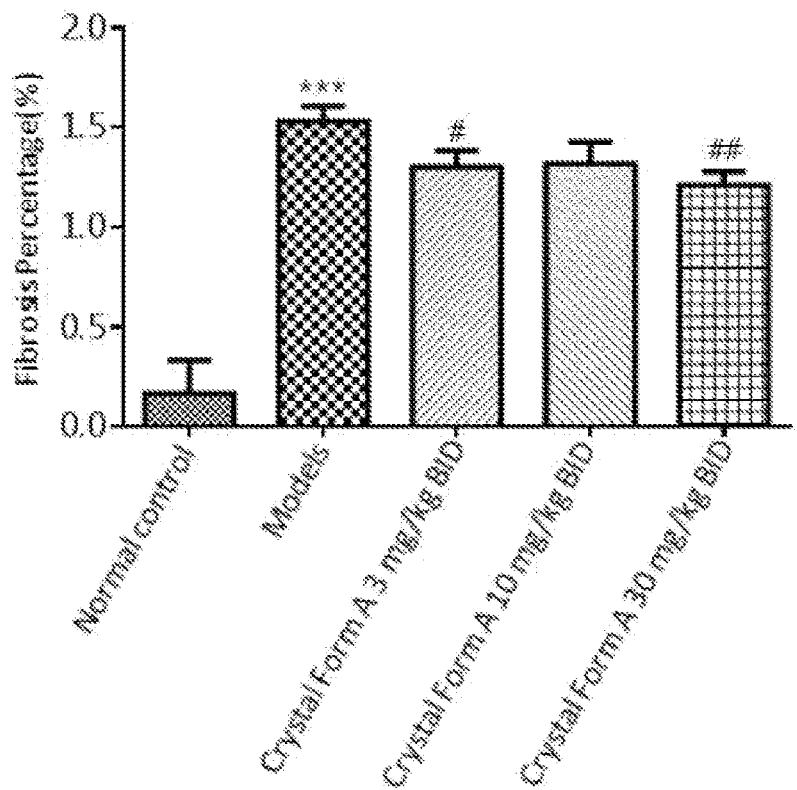
FIG. 14 is a result of an in vivo efficacy test of crystal form A of compound (I) in a CCl4-induced mouse liver fibrosis model; note: * indicates p<0.001 vs. normal control group; #indicates p<0.05 vs. model group; and ##indicates p<0.01 vs. model group.

Effect Example 2 In Vivo Efficacy Test of Crystal Form a of Compound of Formula (I) in CCl4-Induced Mouse Liver Fibrosis Model Experimental Materials:
Male C57BL/6 mice, 22-27 grams in weight, purchased from Shanghai Lingchang Biotechnology Co., Ltd.
Experimental Method:
Mice were transferred to the experimental area after one week of quarantine and adaptation. Animals were randomly divided into groups according to body weight and housed in cages at 5 mice per cage. 20% CCl4 solution with CCl4: Olive oil=1:4 was prepared by dissolving CCl4 in olive oil at a dose of 0.5 μl/g in mice. The mice of model group were orally three times a week for 4 weeks for molding, and the mice of normal control group was administrated only with the same volume of olive oil orally. The subject compounds were administered orally by oral gavage in a volume of 10 ml/kg per animal. The Day 1 of CCl4 modeling was initiated while dosing was initiated until day 28. At the end of the experiment, animal liver samples were collected for histopathological analysis. Whether the molding is successful is determined by comparing a model group with a normal control group; and whether the drug shows a drug effect is determined by comparing the administration group and the model group. The experimental results are shown in FIG. 14.

Experimental Conclusion:

Crystal form A of compound of formula (I) (3 mg/Kg BID, 30 mg/Kg BID) has a significant effect on improving liver fibrosis.

Although the specific embodiments of the present disclosure are described above, those skilled in the art should understand that these are only examples, and various changes or modifications can be made to these embodiments without departing from the principle and essence of the present disclosure. The scope of the present disclosure is, therefore, indicated by the appended claims.

What is claimed is:

1. Crystal form A of a compound of formula (I) having an X-ray powder diffraction (XRPD) pattern with characteristic diffraction peaks at 2θ angles: 8.40±0.2°, 13.46±0.2°, and 14.13±0.2°,

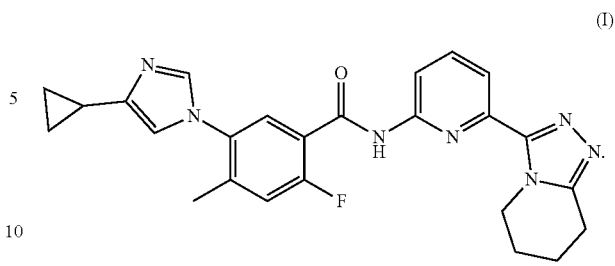

(I)

2. Crystal form A according to claim 1, having an X-ray powder diffraction pattern with characteristic diffraction peaks at 2θ angles: 8.40±0.2°, 10.56±0.2°, 13.46±0.2°, 14.13±0.2°, 15.31±0.2°, 16.79±0.2°, 24.09±0.2° and 24.97±0.2°.

Figure 2:
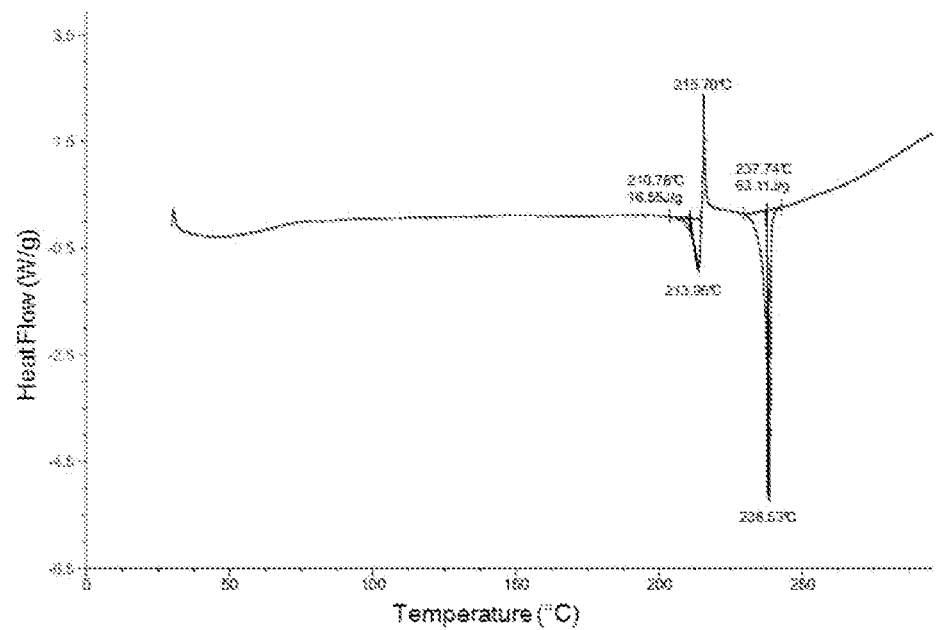
FIG. 2 is a DSC thermogram of crystal form A of compound (I)
Figure 3:
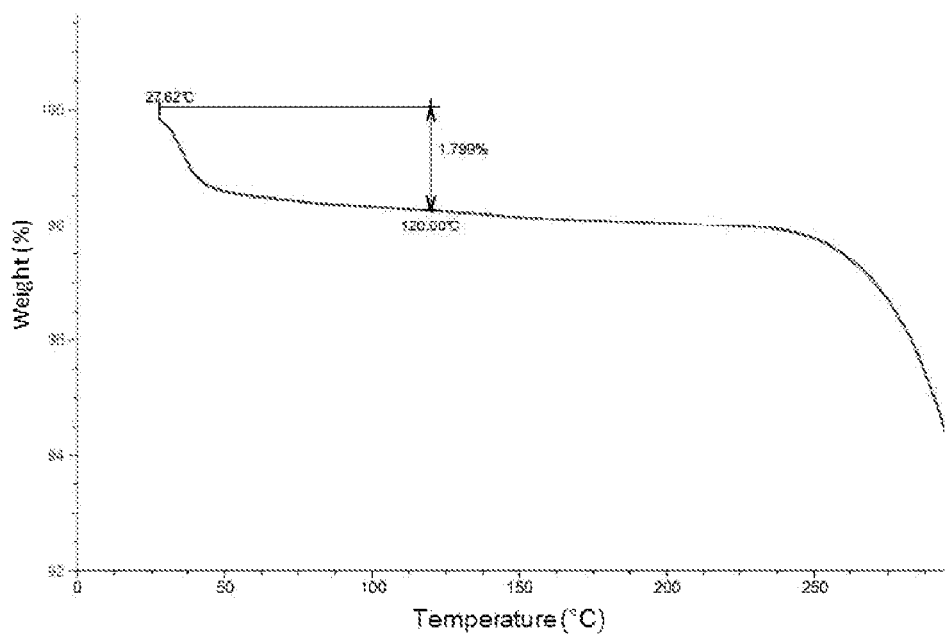
FIG. 3 is a TGA thermogram of crystal form A of compound (I)

3. Crystal form A according to claim 2, having an XRPD pattern as shown in FIG. 1,
   and/or a DSC thermogram as shown in FIG. 2,
   and/or a TGA thermogram as shown in FIG. 3.

4. Crystal form A according to claim 1, having a differential scanning calorimetry curve with two starting points of endothermic peaks at 210.78° C. and 237.74° C., and an exothermic peak at 215.70° C.;
   and/or a thermogravimetric analysis curve with a weight loss up to 1.799% at 120° C.

5. Crystal form B of a compound of formula (I) having an X-ray powder diffraction pattern with characteristic diffraction peaks at 2θ angles: 8.85±0.2°, 17.07±0.2°, and 17.70±0.2°,

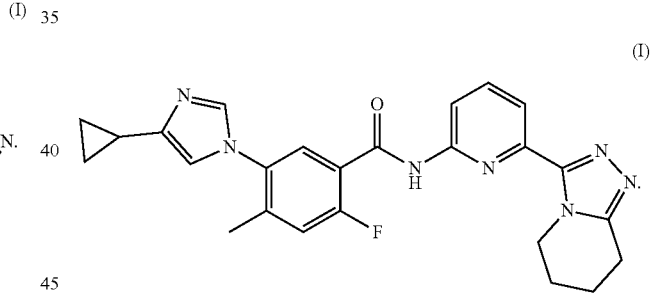

(I)

6. Crystal form B according to claim 5, having an X-ray powder diffraction pattern with characteristic, diffraction peaks at 2θ angles: 8.85±0.2°, 10.20±0.2°, 14.62±0.2°, 17.07±0.2°, 17.70±0.2° 21.57±0.2°, 23 34±0.2" and 24.37±0.2°.

Figure 4:
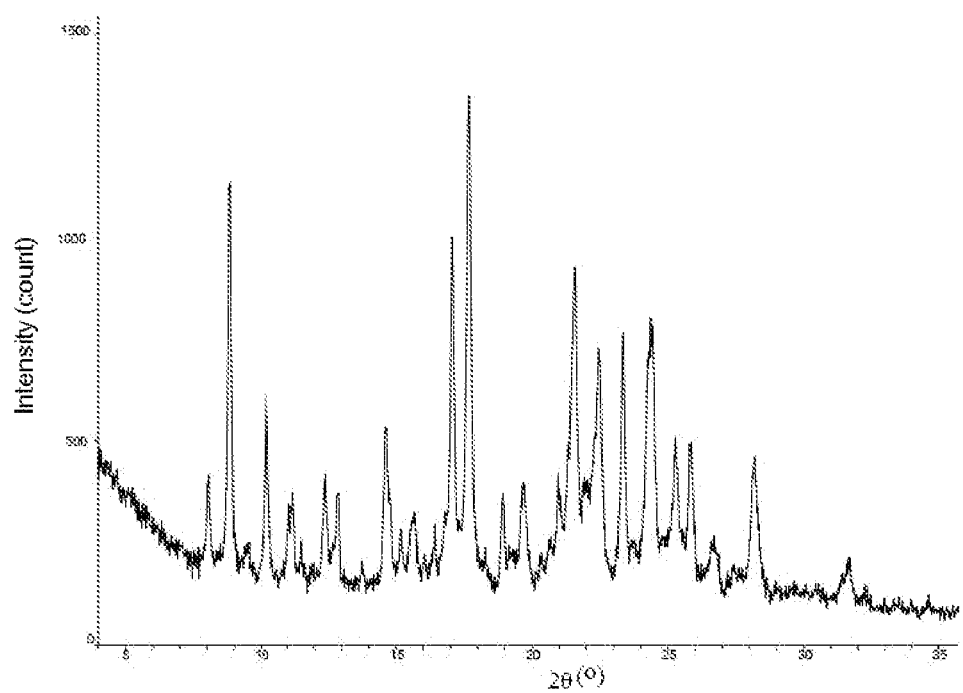
FIG. 4 is an XRPD pattern of Cu-Kα radiation of crystal form B of compound (I)
Figure 5:
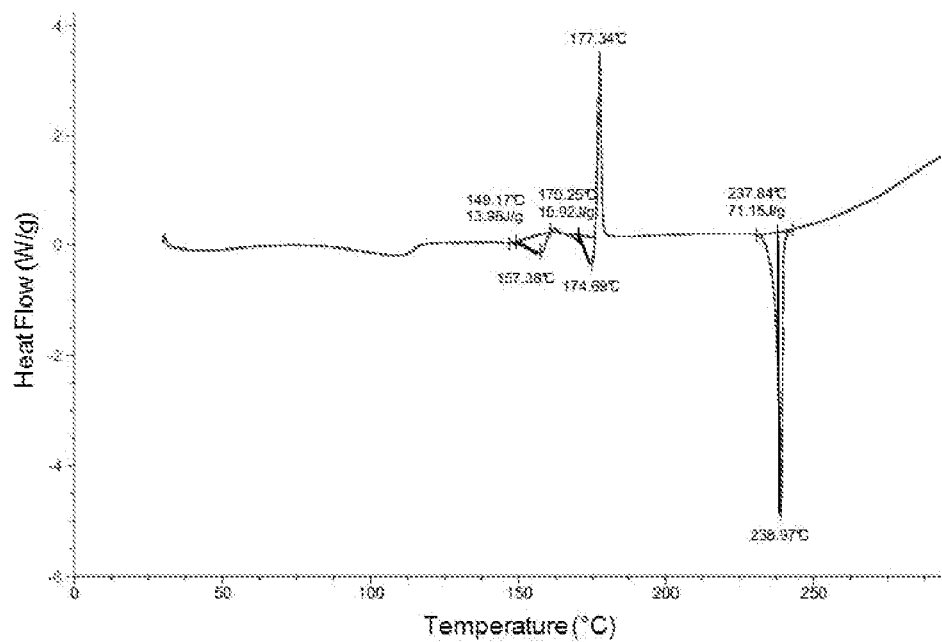
FIG. 5 is a DSC thermogram of crystal form B of compound (I)
Figure 6:
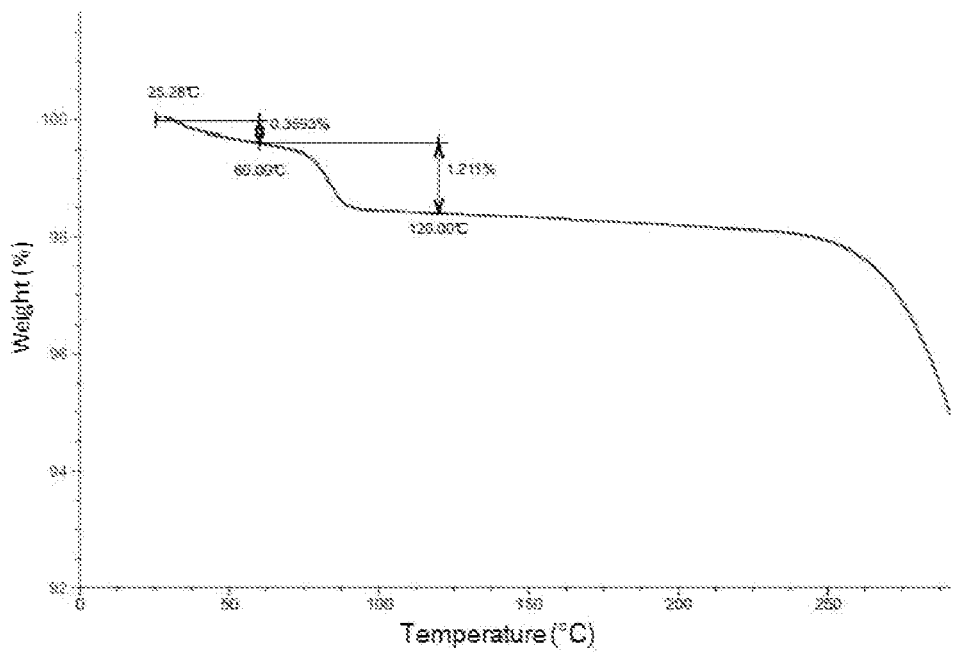
FIG. 6 is a TGA thermogram of crystal form B of compound (I)

7. Crystal form B of claim 6, having an XRPD pattern as shown in FIG. 4,
   and/or a DSC thermogram as shown in FIG. 5,
   and/or a TGA thermogram as shown in FIG. 6.

8. Crystal form B according to claim 5, having a differential scanning calorimetry curve with three starting points of endothermic peaks at 149.17° C., 170.25° C. and 237.84° C., and an exothermic peak at 177.34° C.;
   and/or a thermogravimetric analysis curve with a weight loss up to 0.3593% at 60° C., and a weight loss up to 1.5703% at 120° C.

9. Crystal form C of a compound of formula (I) having an X-ray powder diffraction pattern with characteristic diffraction peaks at 2θ angles: 9.47±0.2°, 16.45±0.2°, and 17.32±0.2°, 10. Crystal form C according to claim 9, having an X-ray powder diffraction pattern with characteristic diffraction peaks at 2θ angles: 8.72±0.2°, 9.47±0.2°, 10.44±0.2°, 13.75±0.2°, 16.45±0.2°, 17.32±0.2°, 19.41±0.2° and 26.82±0.2°.

Figure 7:
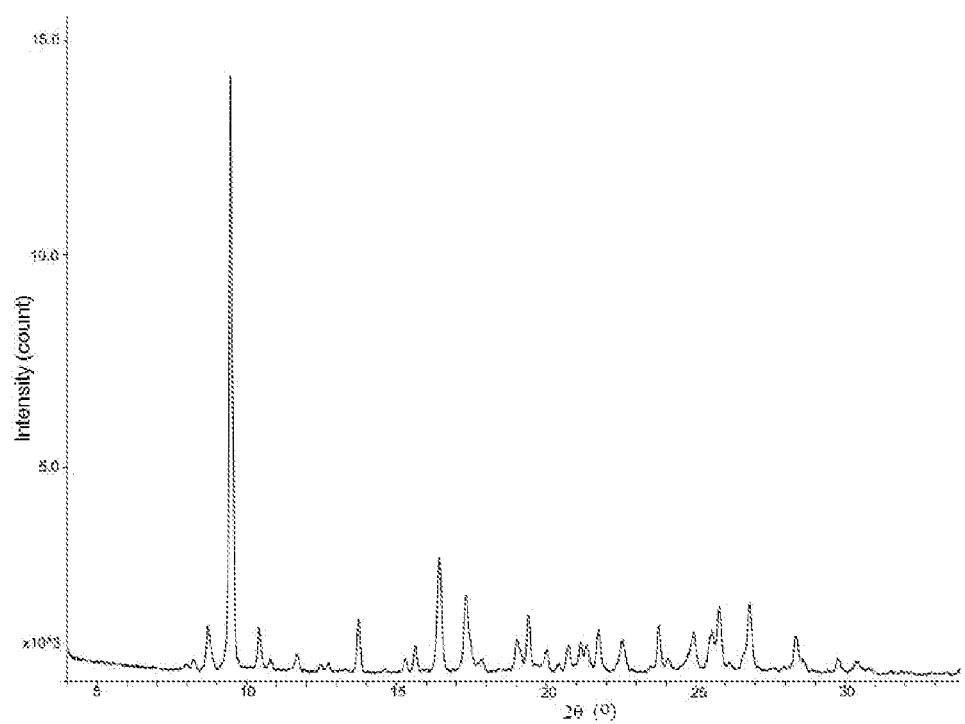
FIG. 7 is an XRPD pattern of Cu-Kα radiation of crystal form C of compound (I)
Figure 8:
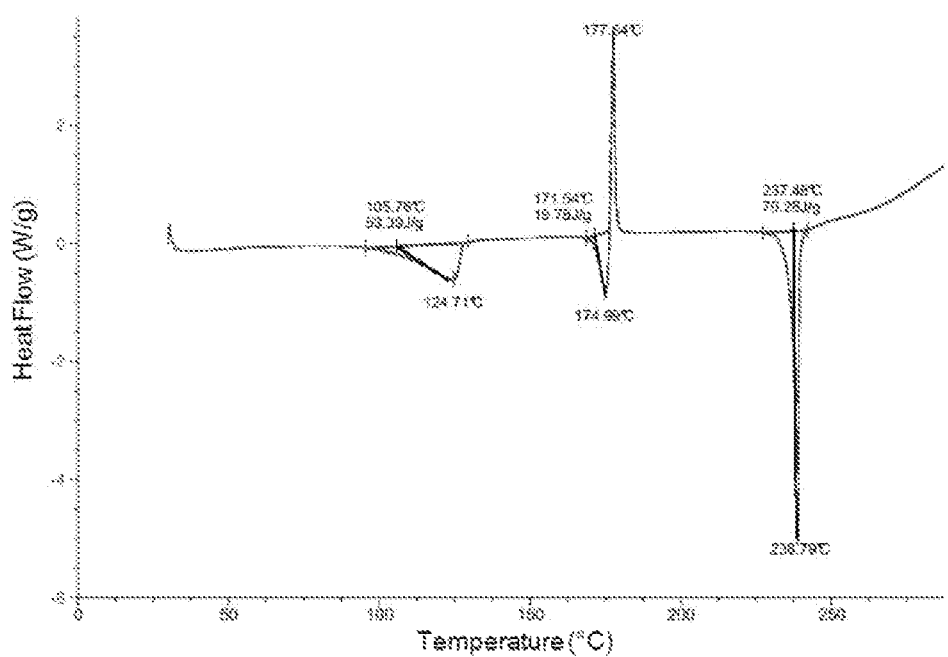
FIG. 8 is a DSC thermogram of crystal form C of compound (I)
Figure 9:
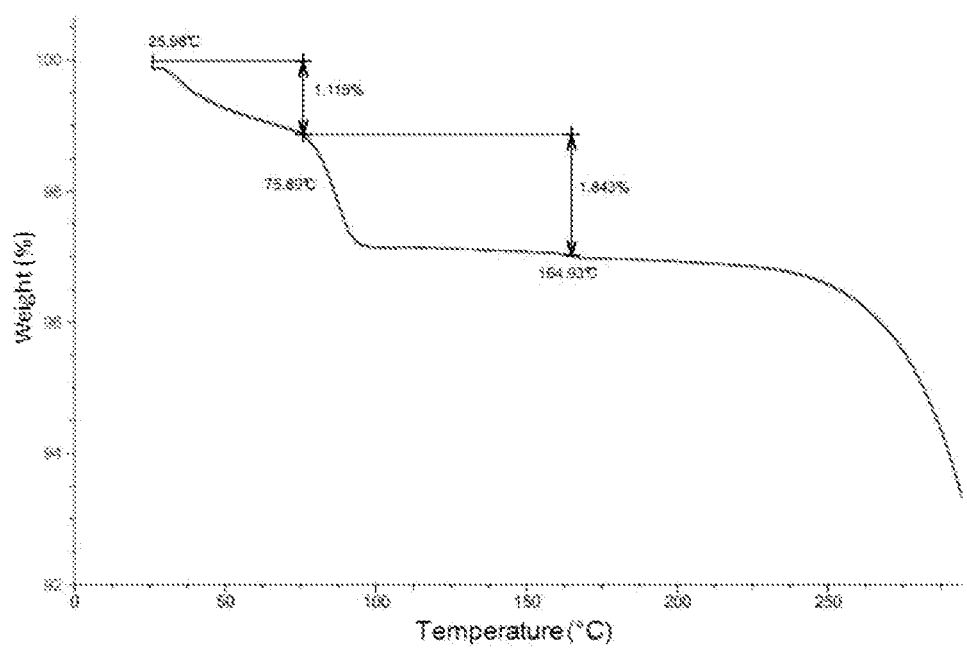
FIG. 9 is a TGA thermogram of crystal form C of compound (I)

11. Crystal form C according to claim 10, having an XRPD pattern as shown in FIG. 7,
    and/or a DSC thermogram as shown in FIG. 8,
    and/or a TGA thermogram as shown in FIG. 9.

12. Crystal form C according to claim 9, having a differential scanning calorimetry curve with three starting points of endothermic peaks at 105.76° C., 171.54° C. and 237.48° C., and an exothermic peak at 177.64° C.;
    and/or a thermogravimetric analysis curve with a weight loss up to 1.115% at 75.89° C., and a weight loss up to 2.958% at 164.93° C.

13. Crystal form D of a compound of formula (I) having an X-ray powder diffraction pattern with characteristic diffraction peaks at 2θ angles: 10.26±0.2°, 12.73±0.2°, and 20.60±0.2°,

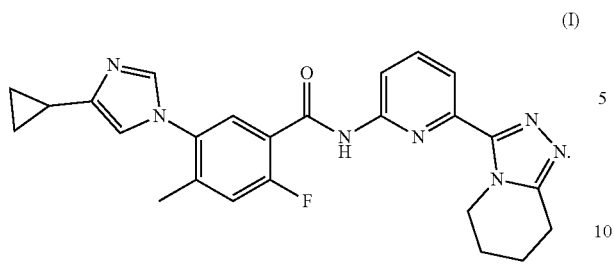

(I)

14. Crystal form D according to claim 13, having an X-ray powder diffraction pattern with characteristic diffraction peaks at 2θ angles: 10.26±0.2θ, 11.84±0.2°, 12.73±0.2°, 14.70±0.2°, 16.39±0.2°, 20.60±0.2°, 21.22±0.2° and 22.26±0.2°.

Figure 10:
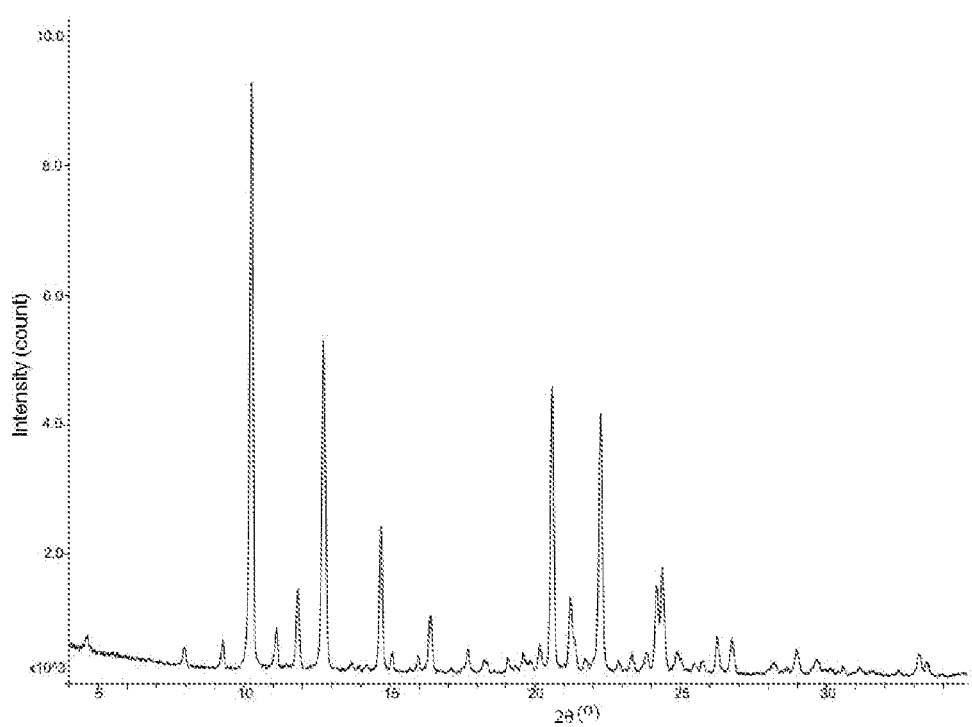
FIG. 10 is an XRPD pattern of Cu-Kα radiation of crystal form D of compound (I)
Figure 11:
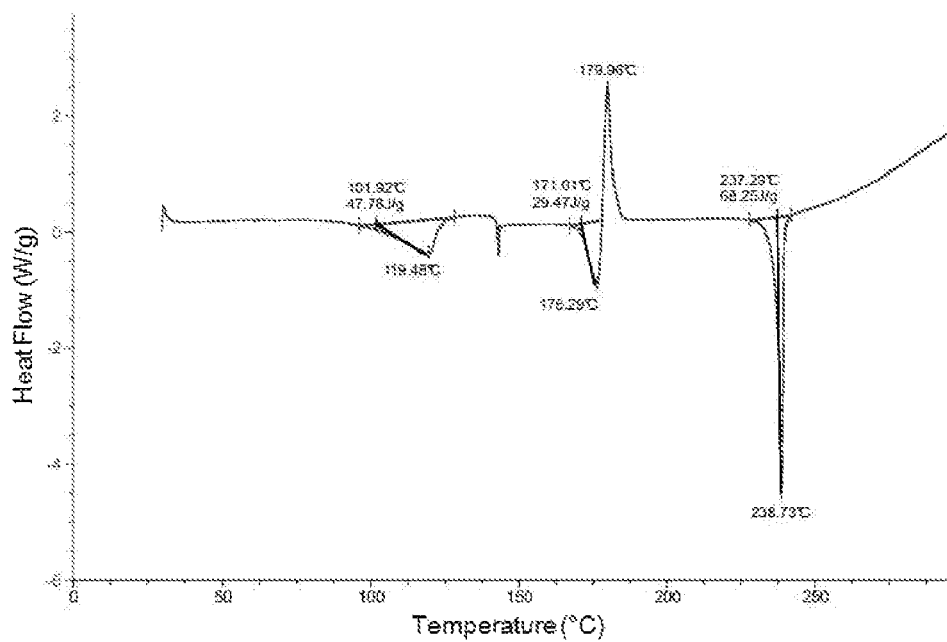
FIG. 11 is a DSC thermogram of crystal form D of compound (I)
Figure 12:
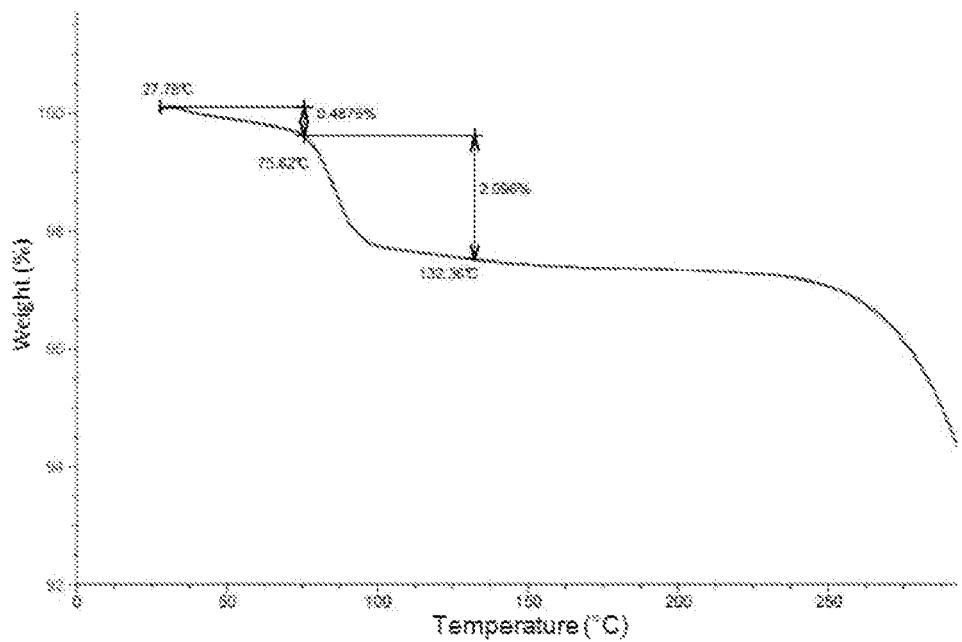
FIG. 12 is a TGA thermogram of crystal form D of compound (I)

15. Crystal form D according to claim 14, having an XRPD pattern as shown in FIG. 10,
and/or a DSC thermogram as shown in FIG. 11,
and/or a TGA thermogram as shown in FIG. 12.

16. Crystal form D according to claim 13, having a differential scanning calorimetry curve with three starting points of endothermic peaks at 101.92° C., 171.01° C. and 237.29° C., and an exothermic peak at 179.96° C.;
and/or a thermogravimetric analysis curve with a weight loss up to 0.4876% at 75.62° C., and a weight loss up to 2.5836% at 132.36° C.

* * * * *